(12) United States Patent
Chiodo et al.

(10) Patent No.: US 9,161,796 B2
(45) Date of Patent: Oct. 20, 2015

(54) MEDICAL DEVICES FOR USE DURING ANKLE FUSION SURGERY

(75) Inventors: Christopher Chiodo, Walpole, MA (US); Brent G. Parks, West Friendship, MD (US); Eric M. Bluman, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 319 days.

(21) Appl. No.: 13/329,281

(22) Filed: Dec. 17, 2011

(65) Prior Publication Data

US 2012/0215223 A1   Aug. 23, 2012

Related U.S. Application Data

(60) Provisional application No. 61/424,640, filed on Dec. 18, 2010.

(51) Int. Cl.
| A61B 17/88 | (2006.01) |
| A61B 17/56 | (2006.01) |
| A61B 17/17 | (2006.01) |
| A61B 17/80 | (2006.01) |
| A61B 17/90 | (2006.01) |

(52) U.S. Cl.
CPC ............... *A61B 17/88* (2013.01); *A61B 17/17* (2013.01); *A61B 17/171* (2013.01); *A61B 17/1728* (2013.01); *A61B 17/56* (2013.01); *A61B 17/808* (2013.01); *A61B 17/8061* (2013.01); *A61B 2017/1775* (2013.01); *A61B 2017/564* (2013.01); *A61B 2017/90* (2013.01)

(58) Field of Classification Search
CPC .. A61B 17/17; A61B 17/171; A61B 17/1728; A61B 2017/1775; A61B 17/8061; A61B 17/808; A61B 2017/90; A61B 17/56; A61B 2017/564; A61B 17/88
USPC .............. 606/70–71, 96, 280–281, 286
See application file for complete search history.

(56) References Cited

U.S. PATENT DOCUMENTS

| 6,572,620 | B1 | 6/2003 | Schon et al. |
| 7,608,075 | B2 | 10/2009 | Tornier |
| 8,057,520 | B2 | 11/2011 | Ducharme et al. |
| 8,114,091 | B2 | 2/2012 | Ratron et al. |
| 8,187,308 | B2 * | 5/2012 | Mullaney et al. ............. 606/281 |
| 8,328,809 | B2 * | 12/2012 | Wenk et al. .................... 606/71 |
| 8,657,820 | B2 | 2/2014 | Kubiak et al. |
| 8,715,363 | B2 | 5/2014 | Ratron et al. |
| 2004/0039394 | A1 | 2/2004 | Conti et al. |
| 2005/0107791 | A1 | 5/2005 | Manderson |

(Continued)

FOREIGN PATENT DOCUMENTS

| FR | 2924593 A1 * | 6/2009 | ............. A61B 17/80 |
| WO | WO 2007131287 A1 * | 11/2007 | ............. A61B 17/80 |

OTHER PUBLICATIONS

Wright Medical publication FA309-509, Wright Medical Technology Inc., Arlington TN. http://www.wmt.com/footandankle/pdf/FA309-509_VALOR_ST.pdf published 2011.

(Continued)

*Primary Examiner* — Larry E Waggle, Jr.
(74) *Attorney, Agent, or Firm* — Law Office of: Michael A. Sanzo, LLC (57) ABSTRACT

The present invention is directed to devices and methods that can be used in ankle surgery, especially ankle fusion surgery.

20 Claims, 4 Drawing Sheets

(56) References Cited

U.S. PATENT DOCUMENTS

| | | |
|---|---|---|
| 2007/0123857 A1 | 5/2007 | Deffenbaugh et al. |
| 2007/0276401 A1* | 11/2007 | Choe et al. ........... 606/96 |
| 2009/0143825 A1* | 6/2009 | Graham et al. ........ 606/286 |
| 2009/0157086 A1* | 6/2009 | Digeser et al. ........ 606/96 |
| 2009/0248084 A1* | 10/2009 | Hintermann ........... 606/286 |
| 2010/0262150 A1* | 10/2010 | Lian ..................... 606/87 |
| 2013/0172942 A1 | 7/2013 | Lewis et al. |
| 2014/0066996 A1 | 3/2014 | Price et al. |
| 2014/0107798 A1 | 4/2014 | Jeng et al. |

OTHER PUBLICATIONS

INTEGRA Mid & Hindfoot Solutions, Integra LifeSciences Corporation. www.ilstraining.com/mid%20%20hindfoot%20solutions/panta/panta_14.html published 2010.

Tornier TTC Plates, http://www.tornier-us.com/lower/ankle/anktra004/, downloaded Nov. 7, 2014.

* cited by examiner

MEDICAL DEVICES FOR USE DURING ANKLE FUSION SURGERY

CROSS REFERENCE TO RELATED APPLICATIONS

The present application claims the benefit of U.S. provisional application 61/424,640 filed on Dec. 18, 2010. This prior application is hereby incorporated by reference in its entirety.

FIELD OF THE INVENTION

The present invention is directed to a contoured fusion plate that can be used during ankle and hindfoot surgery to hold and compress bones together in a fixed position. In addition, the invention encompasses medical devices that include a plate that incorporates a supplemental screw guide that attaches to the plate. The latter is used to position supplemental screws that help immobilize the bones secured by the plate and to ensure that the supplemental screws can be inserted without interfering with other screws that are inserted through the plate.

BACKGROUND OF THE INVENTION

Ankle and hindfoot fusion surgery is a standard orthopedic operation for relieving pain associated with joint degeneration due to such disorders as osteoarthritis, inflammatory arthritis, post-traumatic arthritis, deformity, neuroarthropathy, infection, or rheumatoid arthritis. The procedure typically involves removal of the worn out portion of the joint, followed by the immobilization of bones using an external fixator or an intramedullary device (see generally US 20070123857, published May 31, 2007 and US 20040039394, published Feb. 26, 2004).

Wright Medical began marketing a device in 2010 that uses an elongated metal shaft (a "nail") inserted longitudinally into the tibia of a patient (see Wright Medical publication FA309-509, Wright Medical Technology Inc., Arlington, Tenn.). Screws are positioned using a targeting guide that attaches to the end of the nail and rotates externally around the ankle of a patient. The screws are then inserted to connect and compress bones.

Another device has been described by Schon, et al., which also uses an intramedullary nail inserted into the tibia of patients (U.S. Pat. No. 6,572,620). Stabilizing screws are aligned with holes in the nail through the use of a tower section that extends externally from the base of the nail upward. Screws for joining bones together are positioned using an elongated blade that is driven through the calcaneus bone and intersects the intramedullary nail at a chosen angle.

Although the methods presently used for ankle and hindfoot fusion are effective, a need remains for new devices that can be conveniently used for promoting bone fusion with anatomic rigid plate fixation and the least trauma possible.

SUMMARY OF THE INVENTION

In the description that follows, reference numerals are provided that are shown in the attached figures. It will be understood that the figures illustrate a preferred embodiment of the invention and that variations in design that would be apparent to those of skill in the art are included within the scope of the invention. The figures and reference numerals help to clarify inventive concepts but are not limiting.

Figure 1:
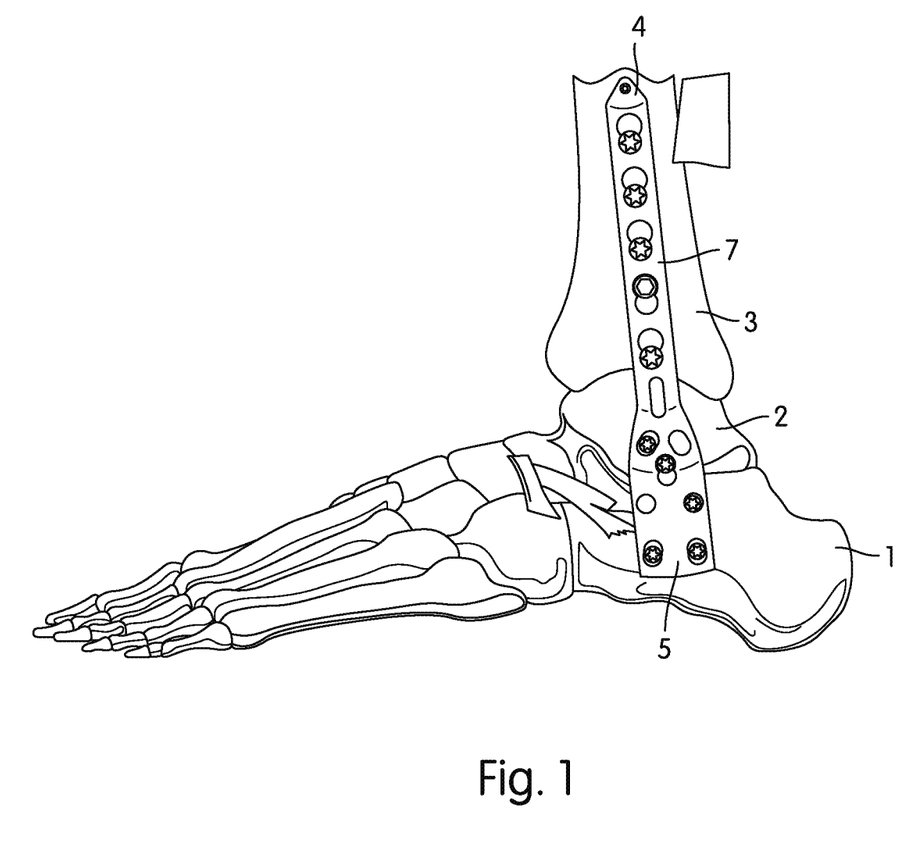
FIG. 1 is a side view of a patient's ankle showing the positioning of the contoured fusion plate during surgery. The fusion plate is positioned on the patient's leg and runs longitudinally along the length of the tibia (3) over the talus (2) and calcaneus (1). It has a proximal end (4), a distal end (5) and a rectangular elongated longitudinal member (7) extending between these two ends. The top surface of the fusion plate faces outward in the figure and the bottom surface is in contact with the patient's leg. For simplicity, the fibula is not shown in the figure.
Figure 2:
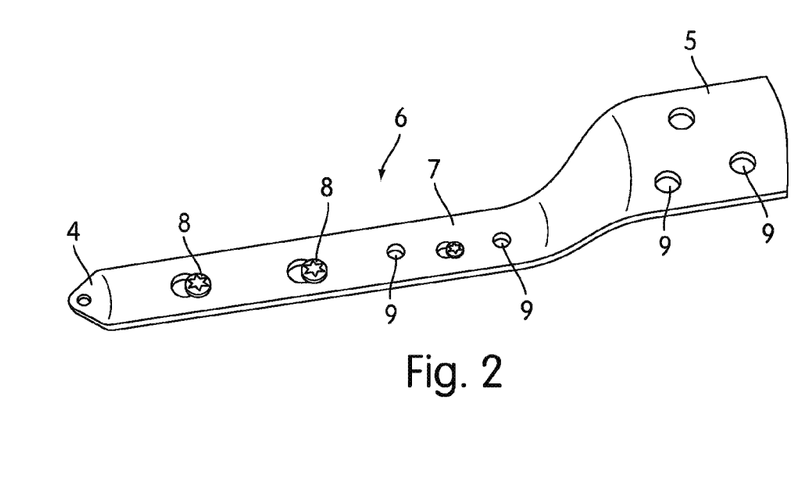

In its first aspect, the invention is directed to a contoured fusion plate (FIG. 2 (6)) comprising a proximal end (FIG. 1 (4)) and a distal end (5) that are connected by an elongated, longitudinal member (7). In the context of the present invention, the term "contoured" means that the fusion plate is shaped in a manner that conforms to, and makes contact with a patient's body and, in this embodiment, with both the relatively straight portion of a patient's leg occupied by the tibia and with the more curved portions of a patient's ankle and hindfoot. The term "longitudinal" as used in connection with the contoured fusion plate refers to the extended member that is oriented in an essentially vertical position lengthwise along a patient's tibia during surgery. The proximal end of the contoured fusion plate, i.e., the end that will be positioned furthest away from a patient's ankle when the fusion plate is in use (see FIG. 1(4)) and the elongated longitudinal member (7) are together in a single plane in the figure but, in some embodiments may also be in somewhat different planes, e.g., if the more proximal end of the plate is bowed, cupped or spoon-shaped. The distal end of the fusion plate (5), i.e., the portion located over a patient's ankle when the device is in use, is displaced in a direction away from the plane formed by the elongated member so that it lies in a different plane to accommodate the protrusion of the ankle and hindfoot (FIG. 2). The device has at least one hole (9) that traverses the elongated longitudinal member of the fusion plate and at least one hole (9) that traverses the distal end of the fusion plate. These allow screws to be inserted that anchor the elongated longitudinal member to the tibia of a patient and that hold the bones of the ankle and hindfoot in fixed position relative to the tibia. In order to facilitate the compression of bones, at least some of the holes in the fusion plate may preferably be obliquely shaped. This allows compression at the fusion site by allowing the fusion plate and/or bone segments to be mobilized towards each other before final fixation is obtained.

The surface of the elongated longitudinal member contacting the leg of a patient, i.e., the "bottom" or "medial" surface, may have an essentially flat bottom or, preferably, may have an essentially concave shape to allow it to better conform to the surface of a patient's leg. The opposite surface may be essentially flat or essentially convex to follow the pattern of the bottom surface. In some embodiments, one or more screws or pegs (8) may protrude from the top surface and serve in connecting an attachable supplemental screw guide (10). The elongated longitudinal member (7) will typically be essentially rectangular with dimensions of 1.0-15 inches in length as measured along its longitudinal axis and 0.5-2.5 inches in width. The distal end of the device (5) will typically be 2.5-6.0 inches in length and 0.5-2.5 inches in width. In some embodiments, the distal end may be wider than the elongated longitudinal member, e.g., 0.25-2.0 inches wider. It is expected that, at its furthest point, the distal end of the device (5) will be displaced by 0.25-1.5 inches from the plane formed by the elongated rectangular longitudinal member (see FIG. 2) in order to accommodate the flare of the proximal tibia, the talar and calcaneal bones.

Figure 3:
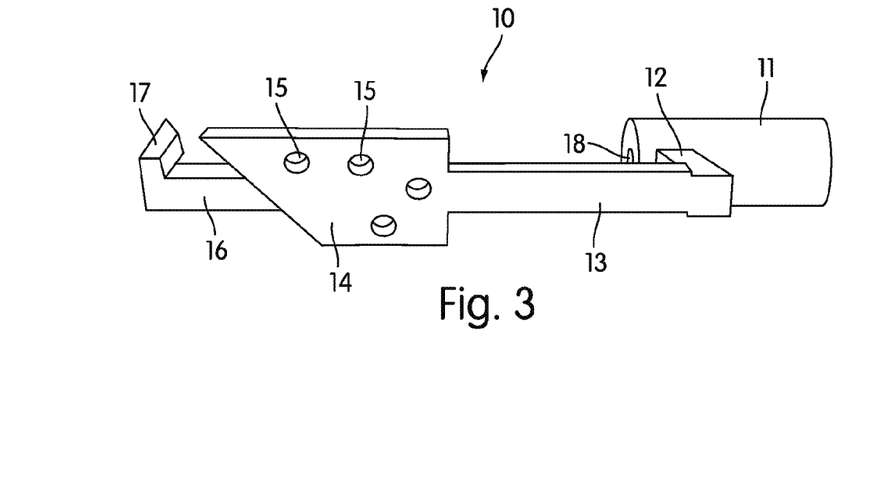
FIG. 3 is an isolated side view of the attachable supplemental screw guide (10) with the front surface (i.e., the surface facing away from a patient's leg when the device is in use during surgery) facing outward. At one end, the supplemental screw guide has a cylindrical drill guide (11) with a channel (18) running completely through it. The drill guide is attached to a planar, elongated guide member (13) by a displacement element (12) that positions the drill guide away from (medially to) the elongated guide member (e.g., by 0.25-1.5 inches). The displacement allows the drill guide to be positioned over the heel of the patient (see FIG. 4). The elongated guide member (13) ends in a broadened mounting plate (14) that is in the same plane as the elongated guide member and that has holes (15) that can engage the pegs or screws in the elongated longitudinal member of the contoured fusion plate for mounting. Extending from the mounting plate (15) is a tibia engagement arm (16) that is essentially in line with the elongated guide member (13). The tibia engagement arm terminates in a tibia contact section (17). This extends approximately perpendicularly from the plane formed by the tibia engagement arm (16), mounting plate (15) and elongated guide member (13).
Figure 4:
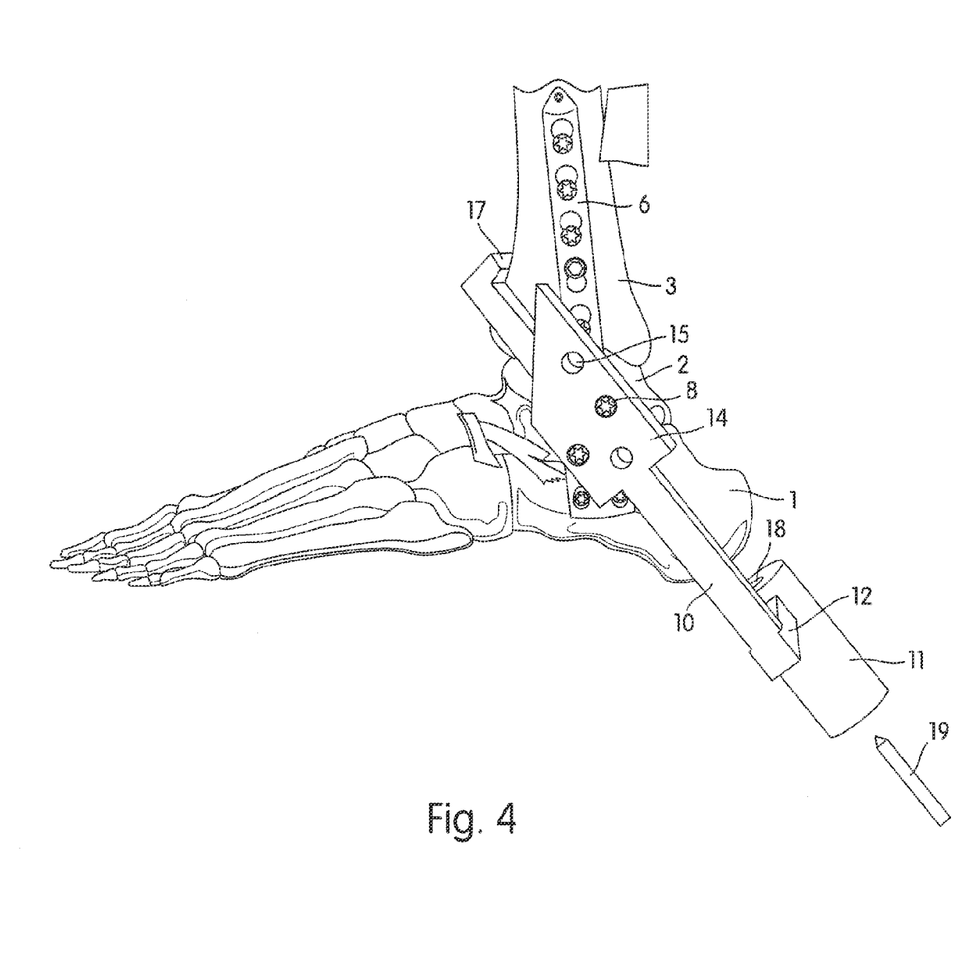
Figure 5:
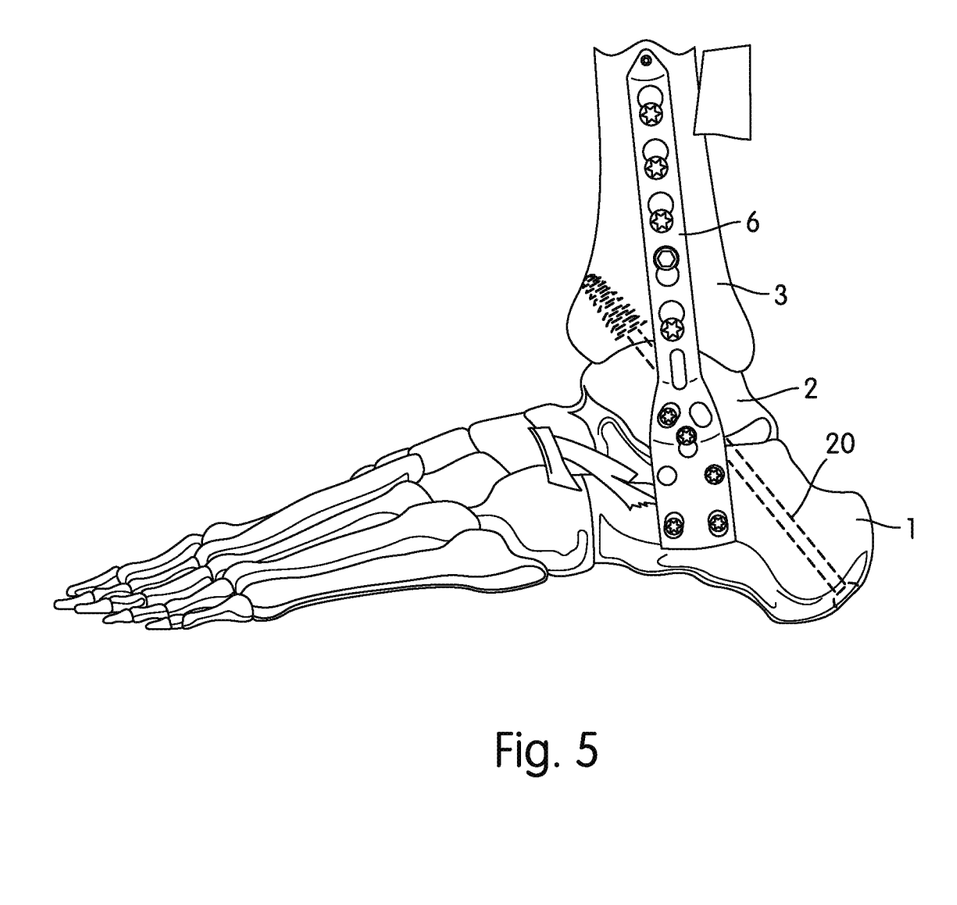
FIG. 5 shows the results of a completed operation in which a supplemental screw has been inserted into a patient. It can be seen that this screw (20) has been passed through the calcaneus (1), talus (2) and tibia (3) to stabilize and draw together these bones.

In a second aspect, the invention is directed to a medical device that includes a contoured fusion plate (6) as described above and an attached supplemental screw guide (see FIG. 3, (10)). The latter is used to position supplemental screws, i.e., screws that are inserted to connect different bones or bone segments/fragments together (see FIG. 5, (20)). The supplemental screw guide (10) includes an elongated guide member (see FIG. 3 (13)) with a mounting apparatus/plate/member (14) that contains means (15) for attaching the supplemental screw guide to the contoured fusion plate. Methods for attachment include the use of screws or pegs located on one surface that interface with holes or slots on the plate. It will be understood however that any type of clamp or shaping that achieves the objective of mounting the supplemental screw guide to the contoured fusion plate can be used. The elongated guide member (13) and mounting plate (14) have a rear surface that, when in use during surgery, faces, and may contact, the contoured fusion plate and an opposite front surface. A drill guide (11) is attached to one end of the elongated guide member (13) by a displacement element (12) that extends away from a plane formed by the front surface of the elongated guide member (13) and mounting plate (14) in the direction of the attached contoured fusion plate (see FIG. 4 (12)). The purpose of the displacement element is to move the drill guide (11) to a desired position (e.g., behind the heel of a patient as shown in FIG. 4) and, ultimately, to orient a long supplemental screw so that it can be inserted from the posterior aspect of the calcaneus to the distal-anterior surface of the tibia without interference with other screws securing the fusion plate to the bones. In addition, there is a tibia engagement arm (FIG. 3 (16)) that extends from the mounting plate (14) of the elongated guide member (13) in a direction essentially parallel to its longitudinal axis. This terminates in a tibia contact section (FIG. 3 (17) that extends in an essentially perpendicular direction from the plane formed by the front surface of the elongated guide member (13) and mounting plate (14) in the direction of the attached contoured fusion plate, i.e., in the same direction as the displacement of the drill guide (see FIG. 4).

The devices described above may be used to improve existing ankle and hindfoot operations. For example operations in which there is the resection and immobilization of bones to promote fusion may be improved by using the contoured fusion plates in place of less anatomic and more invasive devices. The insertion of one or more supplemental screws to connect bones together may also be improved by positioning these screws using the medical device described above. One set of screws (the ones that hold the plate on the bone) are, preferably, locking screws and create a fixed-angle fusion device. The guide then goes onto the plate and allows positioning of a long, augmenting screw. The guide allows this screw to be positioned without it hitting or impinging on the already placed locking screws in the plate.

More generally, the invention includes methods of joining bones together during ankle and hindfoot surgery on a patient by: a) surgically resecting the bones to be joined; b) positioning an elongated contoured fusion plate externally along the tibia of the patient so that the longitudinal axis of the fusion plate is parallel to the longitudinal axis of the tibia and so that the distal end of the device covers at least one bone in the ankle and/or hindfoot (see FIG. 1); c) attaching the elongated contoured fusion plate to the tibia using screws, preferably self-locking screws, that traverse holes in the fusion plate and transversely penetrate the tibia; d) attaching the elongated contoured fusion plate to one or more bones in the ankle and hindfoot using screws that traverse holes in the distal end of the fusion plate and that transversely penetrate the bones; and e) allowing the elongated contoured fusion plate to remain in place connecting the tibia to one or more ankle bones until new bone has grown that fuses the bones together. Most typically, the bones joined will be the tibia, the talus and/or the calcaneus.

The invention also includes methods in which supplemental screws are used to join bones together during ankle surgery or other orthopedic procedures (including fusion, fracture repair, realignment, and osteotomy surgery) in other anatomic locations on a patient. In this case, the method involves: a) surgically resecting the bones to be joined; b) positioning an elongated contoured fusion plate externally along the tibia of the patient so that the longitudinal axis of the fusion plate is parallel to the longitudinal axis of the tibia and so that the fusion plate extends over at least one bone in the ankle (see FIG. 1); c) attaching the elongated contoured fusion plate to the tibia using screws that traverse holes in the fusion plate and transversely penetrate the tibia; d) attaching the fusion plate to one or more bones in the ankle using screws that traverse holes in the distal end of the device and transversely penetrate the ankle bones; e) attaching a supplemental screw guide to the contoured fusion plate (see FIG. 4) and using this guide to position one or more supplemental screws that penetrate the bones to be joined; and f) inserting the supplemental screws so as to connect the bones (see FIG. 5). Unless the patient becomes symptomatic, the elongated contoured fusion plate will typically be allowed to remain in place connecting the tibia to one or more ankle bones until new bone has grown to fuse the bones together. The bones that will most typically be joined will be the tibia, the talus and/or the calcaneus. Preferably this method will be carried out using the elongated contoured fusion plates and supplemental screw guides described above.

BRIEF DESCRIPTION OF THE DRAWINGS

A preferred device of the present invention is illustrated in FIGS. 1-5 along with anatomical information that helps in understanding how the device may be used. The elements shown in the drawings are as follows:

1: calcaneus;
2: talus;
3: tibia;
4: proximal end of the contoured fusion plate;
5: distal end of the contoured fusion plate;
6: contoured fusion plate;
7: elongated longitudinal member of the contoured fusion plate;
8: screws or pins in the elongated longitudinal member of the contoured fusion plate;
9: holes in the contoured fusion plate, one or more of which are obliquely shaped to allow the plate to slide and thereby apply compression to bones;
10: attachable supplemental screw guide;
11: drill guide;
12: displacement element connecting the drill guide to the elongated guide member of the attachable supplemental screw guide;
13: elongated guide member of the attachable supplemental screw guide;
14: mounting plate of the attachable supplemental screw guide;
15: holes in the mounting plate of the attachable supplemental screw guide;
16: tibia engagement arm;
17: tibia contact section of the tibia engagement arm;
18: channel running through the drill guide;
19: drill sheath or guide pin that can be passed through the channel in the drill guide;
20: supplemental screw.

FIG. 2 is an isolated view at a downward angle showing the contoured fusion plate (6) with the top surface being visible. The proximal end (4) and elongated longitudinal member (7) are together in a single plane whereas the distal end (5) is displaced so that it is in a slightly elevated, approximately parallel plane (typically between 0.25 and 1 inch above the plane formed by the proximal end (4) and elongated member (7). The displacement is made to accommodate the outward bulge of the ankle relative to the tibia. The fusion plate may have screws or pegs (8) that are slightly elevated in order to engage holes in the mounting plate of the attachable supplemental screw guide and holes (9) that can accommodate locking screws that attach the fusion plate to the patient's bones. At least some of these holes are, preferably, obliquely shaped to allow the fusion plate to be slid in a manner that compresses bones.

FIG. 4 shows the surgical positioning device as it would be used during ankle surgery. The contoured fusion plate (6) is attached to the tibia (3) of a patient. The attachable supplemental screw guide (10) has been connected by holes (15) in the mounting plate (14) to screws or pegs (8) on the contoured fusion plate (6). The tibia contact section (17) is in contact with the tibia (3) and the cylindrical drill guide (11) is positioned so that the channel running through it (18) is over the calcaneus (1) and is pointed in a direction that passes linearly through the patient's calcaneus (1), talus (2) and tibia (3). The figure also shows a drill sheath (19) that can be passed through the channel (18) in the drill guide (11) to contact the patient's heel and ensure proper drilling.

DETAILED DESCRIPTION OF THE INVENTION

A. Making of Devices

The contoured fusion plate and attached supplemental screw guide described herein can be produced using ordinary procedures and materials well known in the field of medical devices. Typically devices will be made of metal but other rigid materials could also be used. It will be recognized by those of skill in the art that many variations in design are available that result in a device that is substantially the same as those described herein. Variations that represent a design choice and that do not fundamentally alter the properties of the devices are included within the scope of the invention.

B. Surgical Techniques

The present devices can be used in existing orthopedic operations in which bones must be immobilized and fixed with respect to one another. Although specifically designed for use in ankle and hindfoot (e.g., "tibiotalacalcaneal") fusion operations the devices could be modified for use in other contexts as well, e.g. in the repair of fractures and in fusion/fracture/osteotomy surgery in other parts of the skeleton.

Procedures using the devices should involve somewhat less trauma to patients than procedures in which intramedullary nails are permanently inserted into bones. In addition, the devices should be easy to use and, from a manufacturing perspective, cost relatively little to produce.

C. Terminology

Unless otherwise indicated, all terminology used herein should be interpreted as it would be understood by one of skill in the relevant art. To the extent that equivalent materials, structures, methods etc, would be recognized by one of skill in the art, these are part of the invention as well. The terms "essentially" and "approximately" are used to indicate a general characteristic of a device, or method. However, a parameter associated with the characteristic may deviate from an absolute amount by a degree that one of skill in the art would recognize as being acceptable with respect to the intended use. For example, a device part that is in essentially a perpendicular direction with respect to the orientation of a second part would be more perpendicular than parallel (i.e., it would not deviate from a right angle by more than 45 degrees) but it would not necessarily be exactly 90 degrees. Similarly, a device part that is essentially parallel to a second part would be more parallel than perpendicular (i.e., it would not form an angle of more than 45 degrees) but it would not necessarily be exactly in line with the second part (i.e., form a zero degree angle).

C. Alternative Devices and Methodology

The present invention is, in its broadest sense, directed to a device that can be used to hold and compress bones together in a fixed position. The specific device described in detail herein is designed for use in connection with the ankle and hindfoot. However, it should be recognized that the basic concepts associated with this device can also be applied to the joining and compression of bones at other anatomical sites as well. For example, a similarly designed device might be used to immobilize a broken wrist or shoulder bone.

The two most essential features of the devices are: a) the presence of a contoured fusion plate that extends between at least two bones; and b) holes, preferably some of which have an oblique shape, that can be used to attach the fusion plate to the bones being joined with screws in a way that holds the bones in a fixed position with respect to one another. Preferably, the device would also include a supplemental screw guide that can be used to position supplemental screws at an angle that will allow them to be inserted to fuse bones together without interfering with screws securing the fusion plate to the bones. Each of the components and characteristics of the devices described herein may also be incorporated either exactly as described or modified in accordance with the context in which an alternative device is being used.

All references cited herein are fully incorporated by reference. Having now fully described the invention, it will be understood by one of skill in the art that the invention may be performed within a wide and equivalent range of conditions, parameters, and the like, without affecting the spirit or scope of the invention or any embodiment thereof.

What is claimed is:

1. A medical device comprising a contoured fusion plate and an attached supplemental screw guide, wherein said contoured fusion plate comprises a proximal end and a distal end that are connected by an elongated longitudinal member, wherein:
   a) the distal end of said contoured fusion plate is displaced laterally away from said elongated longitudinal member to allow room for the protrusion of the bones of the ankle and hindfoot; and
   b) said supplemental screw guide comprises:
      i) an elongated guide member with a mounting plate that can be attached to said contoured fusion plate, wherein said elongated guide member with a mounting plate comprises:
         aa) a rear surface that, when in use during surgery, faces the contoured fusion plate and a front surface that is opposite to this; and
         bb) a drill guide with a channel running through it wherein said drill guide is connected to one end of said elongated guide member by a displacement element that extends away from the elongated guide member and mounting plate in the direction of the attached contoured fusion plate;
      ii) a tibia engagement arm extending from the mounting plate of the elongated guide member in a direction essentially parallel to the longitudinal axis of the elongated guide member and terminating in a tibia contact section that extends away from the elongated guide member and mounting plate in the direction of the attached contoured fusion plate.

2. The medical device of claim 1, wherein said drill guide is cylindrical.

3. The medical device of claim 1, wherein said supplemental screw guide is attached to said contoured fusion plate by means selected from the group consisting of: screws or pegs extending from the surface of one of these components into holes, slots or grooves on the other; and a clamp, or due to shape.

4. The medical device of claim 1, wherein:
   a) said distal end of the contoured fusion plate is 2.5-6.0 inches in length and 0.5-2.5 inches in width; and
   b) said distal end of the contoured fusion plate is, at its furthest point, 0.25-1.5 inches from the longitudinal axis of said elongated longitudinal member.

5. The medical device of claim 4, wherein:
   a) said elongated longitudinal member of the contoured fusion plate is 1.0-15 inches in length as measured along the longitudinal axis and 0.5-2.5 inches in width;
   b) said distal end of the contoured fusion plate is at least 0.5 inches wider than said elongated longitudinal member.

6. A method of joining bones together during ankle surgery on a patient using the medical device of claim 1, said method comprising:
   a) surgically resecting the bones to be joined;
   b) positioning the elongated longitudinal member of said contoured fusion plate externally along the tibia of said patient so that the longitudinal axis of said elongated longitudinal member is essentially parallel to the longitudinal axis of said tibia, and wherein said fusion plate extends at least part way over at least one bone in the ankle;
   c) attaching said contoured fusion plate to said tibia using screws that traverse holes in said contoured fusion plate and transversely penetrate said tibia;
   d) attaching said contoured fusion plate to one or more bones in the ankle using screws that traverse holes in said contoured fusion plate at its distal end and penetrate said one or more bones in said ankle;
   e) using said supplemental screw guide to position one or more supplemental screws so as to penetrate the bones to be joined;
   f) inserting said one or more supplemental screws so as to connect the bones.

7. The method of claim 6, further comprising:
   g) allowing said contoured fusion plate to remain in place connecting said tibia to said one or more ankle bones until new bone has grown in said patient to fuse said tibia to said one or more ankle bones.

8. The method of claim 6, wherein said tibia is fused to the talus of said patient.

9. The method of claim 6, wherein the tibia, talus and calcaneus of said patient are fused together.

10. The method of claim 6, wherein:
    a) the contoured fusion plate of said medical device comprises a distal end that is 2.5-6.0 inches in length and 0.5-2.5 inches in width; and
    b) said distal end of the contoured fusion plate is, at its furthest point, 0.25-1.5 inches from the longitudinal axis of said elongated longitudinal member.

11. The method of claim 6, wherein:
    a) the elongated longitudinal member of the contoured fusion plate of said medical device is 1.0-15 inches in length as measured along the longitudinal axis and 0.5-2.5 inches in width;
    b) the distal end of the contoured fusion plate is at least 0.5 inches wider than said elongated longitudinal member.

12. The method of claim 6, wherein said supplemental screw guide is attached to said contoured fusion plate by means selected from the group consisting of: screws or pegs extending from the surface of one of these components into holes, slots or grooves on the other; and a clamp, or due to shape.

13. A medical device comprising a contoured fusion plate and an attached supplemental screw guide, wherein said contoured fusion plate comprises a proximal end and a distal end that are connected by an elongated longitudinal member, wherein:
    a) the distal end of said contoured fusion plate is displaced laterally away from said elongated longitudinal member to allow room for the protrusion of the bones of the ankle and hindfoot;
    b) said supplemental screw guide comprises an elongated guide member with a mounting plate that can be attached to said contoured fusion plate, and wherein said elongated guide member with a mounting plate has a rear surface that, when in use during surgery, faces the contoured fusion plate and a front surface that is opposite to this; and
    c) said supplemental screw guide further comprises a drill guide which is attached to one end of said elongated guide member by a displacement element that extends away from the elongated guide member and mounting plate in the direction of the attached contoured fusion plate.

14. The medical device of claim 13, wherein at least one hole traverses said elongated longitudinal member and at least one hole traverses the distal end of said contoured fusion plate.

15. The medical device of claim 13, wherein said supplemental screw guide further comprises a tibia engagement arm extending from the mounting plate of the elongated guide member in a direction essentially parallel to the longitudinal axis of the elongated guide member and terminating in a tibia contact section that extends away from the elongated guide member and mounting plate in the direction of the attached contoured fusion plate.

16. The medical device of claim 15, wherein at least one hole traverses said elongated longitudinal member and at least one hole traverses the distal end of said contoured fusion plate.

17. A method of joining bones together during ankle surgery on a patient using the medical device of claim 13, said method comprising:
 a) surgically resecting the bones to be joined;
 b) positioning the elongated longitudinal member of said contoured fusion plate externally along the tibia of said patient so that the longitudinal axis of said elongated longitudinal member is essentially parallel to the longitudinal axis of said tibia, and wherein said fusion plate extends at least part way over at least one bone in the ankle;
 c) attaching said contoured fusion plate to said tibia using screws that traverse holes in said contoured fusion plate and transversely penetrate said tibia;
 d) attaching said contoured fusion plate to one or more bones in the ankle using screws that traverse holes in said contoured fusion plate at its distal end and penetrate said one or more bones in said ankle;
 e) using said supplemental screw guide to position one or more supplemental screws so as to penetrate the bones to be joined;
 f) inserting said one or more supplemental screws so as to connect the bones.

18. The method of claim 17, further comprising:
 g) allowing said contoured fusion plate to remain in place connecting said tibia to said one or more ankle bones until new bone has grown in said patient to fuse said tibia to said one or more ankle bones.

19. The method of claim 17, wherein said tibia is fused to the talus of said patient.

20. The method of claim 17, wherein the tibia, talus and calcaneus of said patient are fused together.

* * * * *